United States Patent
Hans Moore et al.

(10) Patent No.: US 8,642,065 B2
(45) Date of Patent: Feb. 4, 2014

(54) OSTEOGENIC PROMOTING IMPLANTS AND METHODS OF INDUCING BONE GROWTH

(75) Inventors: Meredith Hans Moore, West Chester, PA (US); Doug Buechter, West Chester, PA (US); Melissa Brown, West Chester, PA (US); Lisa Hughes, West Chester, PA (US); Stephen Hornsby, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

(21) Appl. No.: 13/404,097

(22) Filed: Feb. 24, 2012

(65) Prior Publication Data

US 2012/0219599 A1 Aug. 30, 2012

Related U.S. Application Data

(60) Provisional application No. 61/446,706, filed on Feb. 25, 2011.

(51) Int. Cl.
*A61F 2/28* (2006.01)

(52) U.S. Cl.
USPC .......................................................... 424/426

(58) Field of Classification Search
None
See application file for complete search history.

(56) References Cited

U.S. PATENT DOCUMENTS

| | | | |
|---|---|---|---|
| 2002/0082694 A1* | 6/2002 | McKay | ...................... 623/17.11 |
| 2006/0008504 A1 | 1/2006 | Kerr et al. | |
| 2008/0003255 A1 | 1/2008 | Kerr et al. | |

FOREIGN PATENT DOCUMENTS

| | | |
|---|---|---|
| WO | WO 03/105731 | 12/2003 |
| WO | WO 2008/109807 | 9/2008 |
| WO | WO 2009/048270 | 4/2009 |
| WO | WO 2011/123110 | 10/2011 |

OTHER PUBLICATIONS

Aghaloo et al., "Oxysterols Enhance Osteoblast Differentiation In Vitro and Bone Healing In Vivo", Journal of Orthopaedic Research, Nov. 2007, 1487-1497.
Dousa et al., "Cyclic-3'5'-Nucleotide Phosphodiesterase Isozymes in Cell Biology and Pathophysiology of the Kidney", Kidney International, 1999, 55, 29-62.
Kha et al., "Oxysterols Regulate Differentiation of Mesenchymal Stem Cells: Pro-Bone and Anti-Fat", Journal of Bone and Mineral Research, Jan. 2004, 19(5), 11 pages.
Siddappa et al., "cAMP/PKA Activation in Human Mesenchymal Stem Cell in Vitro Results in Robust Bone Formation in Vivo", PNAS, May 2008, 105(20), 6 pages.
Son et al., "Enhancement of the ALP Activity of C3H10T1/2 Cells by the Combination of an Oxysterol and Apatite", Biomedical Materials, Aug. 2010, 6 pages.

* cited by examiner

*Primary Examiner* — Carlos Azpuru
(74) *Attorney, Agent, or Firm* — Woodcock Washburn LLP

(57) ABSTRACT

The present disclosure describes an implant for improving bone growth including an osteoconductive scaffold and an osteoinductive small molecule. The osteoconductive scaffold can further include a polymeric binder. The implant can also include an osteogenic material to provide a viable cell population to assist the bone repair and remodeling. Also disclosed is a system for forming an implant for improving bone growth, as well as methods for forming the implant according to the disclosure, in addition to methods of therapeutic use of the implant.

11 Claims, 14 Drawing Sheets

OSTEOGENIC PROMOTING IMPLANTS AND METHODS OF INDUCING BONE GROWTH

CROSS-REFERENCE TO RELATED APPLICATIONS

This application claims priority to U.S. Provisional Patent Application Ser. No. 61/446,706, filed Feb. 25, 2011, the disclosure of which is hereby incorporated by reference as if set forth in its entirety herein.

FIELD

The present disclosure relates to an implant for promoting bone growth including an osteoconductive scaffold and an osteoinductive small molecule. The implant can further include osteogenic material. Also disclosed is a system for forming an implant as well as a method of treatment utilizing the implant of the present disclosure.

BACKGROUND

Bone fracture repairs and spinal fusions often require a biologic boost to grow bone. Autograft is the most clinically desired treatment option due to its proven safety and efficacy profile. Autograft is osteogenic, osteoinductive and osteoconductive, and comes with zero risk of rejection. However, autograft treatment can present problems due to morbidity issues associated with harvesting the graft from, for example, the patient's iliac crest, and because the needed volume of autograft is not always available. Thus there is an existing clinical need for non-autograft based osteoinductive and osteogenic treatment options.

Osteoinduction is a complex pathway involving multiple layers of redundancy with growth factors, hormones, stem cells and a host of other factors contributing to the process. Current growth factor treatments, such as bone morphogenic proteins (BMPs), are sometimes subject to super-physiological dosing which can have undesired side-effects and may not be the best solution. Osteoinduction treatments have classically been defined by factors or matrices that can stimulate bone growth de novo, for example BMP-2 and BMP-7. Bone healing is a multi-faceted closely coordinated process that involves different cells and biological processes that are controlled and managed through a variety of cellular signaling pathways. Human growth factors, such as BMPs, often drive these pathways and administration of them therapeutically represents one way of impacting bone growth.

However, given the extensive pathways that intersect to trigger bone growth there are potential technologies with osteoinductive properties beyond BMPs.

SUMMARY

The present disclosure is directed towards an implant for promoting bone growth including an osteoconductive scaffold and an osteoinductive small molecule. The scaffold can include autograft material, allograft material, ceramic-based bone substitutes, and blends and mixtures thereof. The osteoinductive small molecule can be selected from corticosteroids, oxysterols, compounds that upregulate intracellular cAMP, and compounds that impact the HMG coA reductase pathway and blends and mixtures thereof.

The implant can further include an osteogenic material. The osteogenic material can be obtained from autogenic or allogenic sources and includes, autograft, autogenic bone marrow aspirate, autogenic lipoaspirate, allogenic bone marrow aspirate, allogenic lipoaspirate, and blends and mixtures thereof.

According to another embodiment, the osteoconductive scaffold is a ceramic bone substitute, such as a calcium-phosphate based compound such as an apatite or tricalcium phosphate, and blends and mixtures thereof. According to a further embodiment, the ceramic bone substitute is a plurality of porous granules having an average granule diameter of about 0.5mm. to about 4.0mm and an average pore diameter of about 20μm to about 500μm.

According to still another embodiment, the scaffold further includes a polymeric binder. The polymeric binder can be a resorbable polymer and can include, for example polylactides, polyglycolides, polylactones, collagen, cellulose, and copolymers, blends and mixtures thereof.

According to the present disclosure, the implant includes an osteoinductive small molecule from a group of compounds such as corticosteroids, oxysterols compounds that upregulate intracellular cAMP, and compounds that impact the HMG coA reductase pathway. Suitable corticosteroids can include, for example budesonide, fluticasone propionate, fluorometholone, halcinonide, clobetasol propionate, and blends and mixtures thereof. According to one embodiment the osteoinductive small molecule can be combined with an excipient. Suitable excipients can include for example, Captisol®(sulfobutylether β- cyclodextrin having the molecular formula $C_{42}H_{70}-nO_{35}$ $(C_4H_8SO_3Na)n$; where n=the average degree of substitution; CAS Number 182410-00-0), Cremphor EL ® (polyethoxylated castor oil, also known as Kolliphor® EL,; CAS Number 61791-12-6), DMA, DMSO, Labrasol®(caprylcaproyl macrogol glycerides), NMP, polyethylene glycol, propylene glycol, PVP, Solutol HS 15® (polyoxyl-15-hydroxystearate; also known as Kolliphor® HS 15; CAS Number 70142-34-6), Tween 20 ® (polyethylene glycol sorbitan monolaurate; CAS Number 9005-64-5) Tween 80 ® (polyethylene glycol sorbitan monooleate; CAS Number 9005-65-6), and mixtures and derivatives thereof.

According to the present disclosure, a method is provided for inducing bone growth in a patient including the step of implanting in the patient an implant according to any of the embodiments of the present disclosure.

According to another embodiment, a method of forming an implant includes the step of combining an osteoconductive scaffold with an osteoinductive small molecule to form an implant. According to a further embodiment, the scaffold can include autograft material, allograft material, ceramic bone substitute, and blends and mixtures thereof, and the synthetic small molecule can include corticosteroids, oxysterols, compounds that upregulate intracellular cAMP, and compounds that impact the HMG coA reductase pathway and blends and mixtures thereof. According to still another embodiment, the method can include the step of combining an osteogenic material to the implant. Suitable osteogenic material can include autograft, autogenic bone marrow aspirate, autogenic lipoaspirate, allogenic bone marrow aspirate, allogenic lipoaspirate, and blends and mixtures thereof. According to yet another embodiment, the method can further include the step of combining the osteoinductive small molecule with an excipient.

The present disclosure also includes a system for forming an implant to promote bone growth including an osteoconductive scaffold housed in a first sterile container having an opening adapted to connect with a second container, an osteoinductive small molecule and an osteogenic material housed in a second sterile container having an opening adapted to connect with the first container such that the osteogenic material can be transferred from the second container to the first container. According to one embodiment of the system the scaffold can include autograft material, allograft material, ceramic bone substitute, and blends and mixtures thereof, the osteoinductive small molecule can include corticosteroids, oxysterols, compounds that upregulate intracellular cAMP, and compounds that impact the HMG coA reductase pathway and blends and mixtures thereof, and the osteogenic material can be derived autograft, autogenic bone marrow aspirate, autogenic lipoaspirate, allogenic bone marrow aspirate, allogenic lipoaspirate, and blends and mixtures thereof. According to another embodiment of the system, the osteoinductive material is included in the first container, and according to a further embodiment the osteoinductive material is included in the second container.

According to one embodiment of the system, the scaffold is a ceramic bone substitute, and in a further embodiment, the scaffold includes a polymeric binder. According to another embodiment the ceramic bone substitute is a calcium-phosphate based compound, such as apatites and tricalcium phosphates, and blends and mixtures thereof, and in still another embodiment the polymeric binder includes polylactides, polyglycolides, polylactones, collagen, cellulose, and copolymers, blends and mixtures thereof.

According to yet another embodiment of the system, the osteoinductive small molecule can includes compounds from the group of corticosteroids including budesonide, fluticasone propionate, fluoromethalone, halcinonide, clobetasol propionate, and blends and mixtures thereof. In still another embodiment of the system, the osteoinductive small molecule can be combined with an excipient. Suitable excipients can include for example, Captisol® sulfobutylether β-cyclodextrin, having the molecular formula $C_{42}H_{70}$-$nO_{35}C_4H_8SO_3Na)n$; where n = the average degree of substitution; CAS Number 182410-00-0), Cremphor EL ® (polyethoxylated castor oil, also known as Kolliphor® EL,; CAS Number 61791-12-6), DMA, DMSO, Labrasol ® (caprvlcaproyl macrogol glycerides), NMP, polyethylene glycol, propylene glycol, PVP, Solutol HS 15 ® (polyoxyl-15-hydroxystearate; also known as Kolliphor® HS 15; CAS Number 70142-34-6), Tween 20 ® (polyethylene glycol sorbitan monolaurate; CAS Number 9005-64-5) Tween 80 ® (polyethylene glycol sorbitan monooleate; CAS Number 9005-65-6), and mixtures and derivatives thereof.

BRIEF DESCRIPTION OF THE DRAWINGS

The foregoing summary, as well as the following detailed description of preferred embodiments of the application, will be better understood when read in conjunction with the appended drawings. It should be understood, however, that the application is not limited to the precise embodiments described. In the drawings.

DETAILED DESCRIPTION

Figure 1:
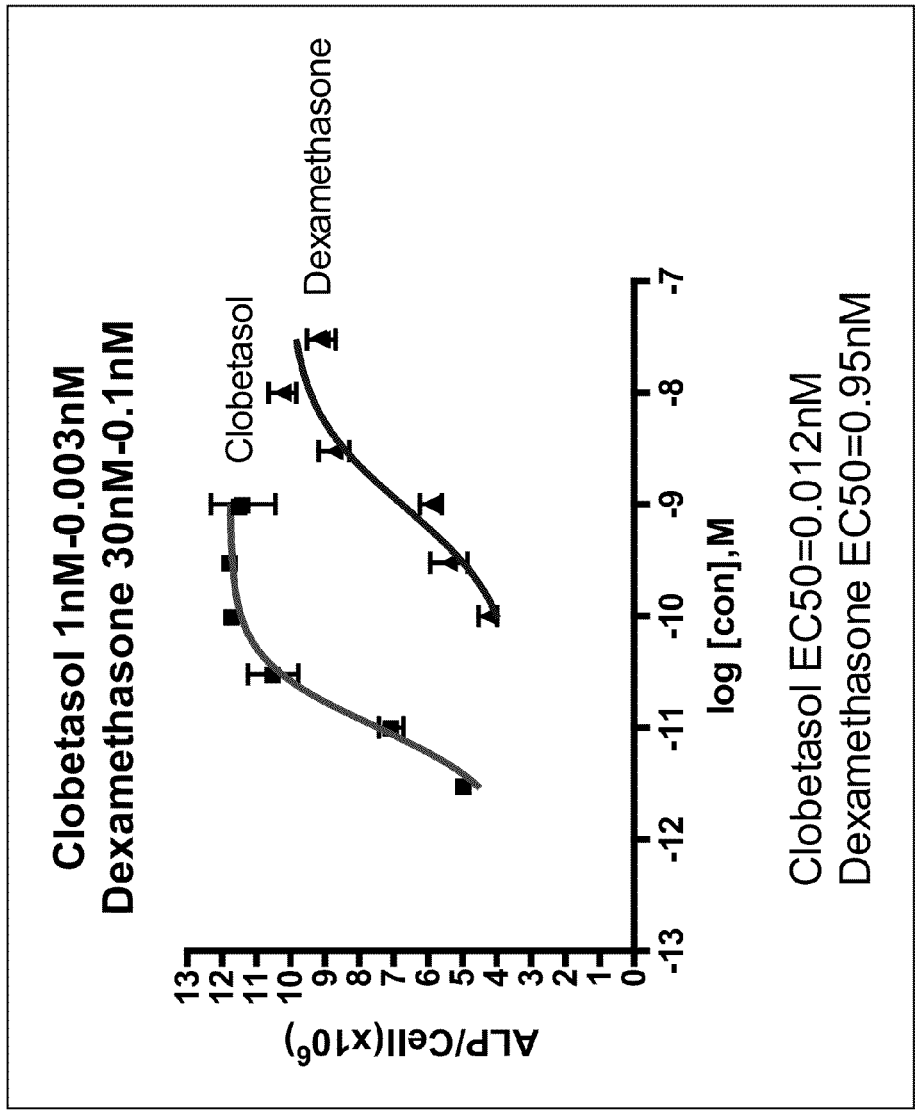
FIG. 1 is a graphical representation of a dose response curve for two small osteoinductive molecules according to embodiments of the present disclosure.

In order that the present disclosure may be more fully understood the following definitions are set forth:

"Osteoconduction" as used herein refers to the process by which an implanted matrix permits or encourages new bone growth on its surface or in its pores, channels, or other internal voids. A graft material or graft matrix is said to be "osteoconductive" when it can serve as a scaffold for new bone growth. Osteoblasts (bone-forming cells) at the defect site of the host bone that is being repaired utilize the implanted graft material as a framework upon which to spread and generate new bone.

"Osteoinduction" as used herein refers to the process of stimulation of osteoprogenitor cells to differentiate into osteoblasts that then begin new bone formation. A chemical or biological composition is said to be "osteoinductive" when it can stimulate primitive, undifferentiated and pluripotent cells into the bone-forming cell lineage.

"Osteogenesis" as used herein occurs when osteoblasts, as well as, osteoprogenitor cells, stem cells, and other cell types capable of differentiating into mature osteoblasts, contribute to new bone growth at the bone graft implant site. A cell or cell population is said to be "osteogenic" if it is capable of differentiation to a mature osteoblast.

"Small Molecule" as used herein, refers to organic molecules that have a relatively low molecular weight (i.e., less than about 800 Daltons) including both naturally occurring and artificially synthesized. As used herein, the term does not include natural or synthetic proteins larger than about 800 Daltons, such as both natural and recombinant based Human Growth Factors or Morphogens, for example Bone Morphogenic Proteins.

"EC50" as used herein refers to the term effective concentration (EC50) that is the concentration of a composition which induces a therapeutic response halfway between the baseline and maximum after some specified exposure time. The EC50 of a graded dose response curve therefore represents the concentration of a compound where 50% of its maximal effect is observed.

"CC50" as used herein refers to the term cytotoxic concentration (CC50) that is the concentration of a compound which induces a cytotoxic response halfway between the baseline and some maximum after some specified exposure time.

"Therapeutic index" (also known as therapeutic ratio), as used herein, is a comparison of the amount of a composition that causes the therapeutic effect to the amount that causes cytotoxic harm. Quantitatively, it is the ratio given by CC50 divided by the EC50. A higher therapeutic index is preferable to a lower one: it would take a much higher dose of such a composition to reach a cytotoxic threshold than the dose taken to elicit the therapeutic effect.

"Excipient" as used herein, refers to pharmacologically suitable inactive substance(s) used in combination with an active agent, e.g., an osteoinductive small molecule, to aid or promote the preparation, administration, delivery, adsorption or absorption of the active agent in a mammalian host.

The present disclosure is directed to an implant for promoting bone growth including an osteoconductive scaffold and an osteoinductive small molecule and can also include an osteoconductive scaffold having a polymeric binder. The implant can further include an osteogenic material. The disclosure is also directed to a method of forming the implant, as well as therapeutic treatment and uses of the implant. Finally, the disclosure is directed to a system for forming the implant including the osteoinductive small molecule, a first container housing the osteoconductive scaffold and a second container housing the osteogenic material, where the second container is adapted to transfer the osteogenic material into the first container.

Osteoconductive scaffolds according to the present disclosure can include autologous bone, allogenic bone, as well as ceramic bone substitutes. Autologous bone can be harvested from bones such as the iliac crest. Autologous bone offers less risk of rejection because it has originated from the patient's own body. Additionally, autologous bone can also provide osteoinductive and osteogenic properties in addition to having osteoconductive properties. Autologous bone scaffolds with high solid bone content has a higher osteoconductive potential than autologous bone that contains a lower solid bone content. Allogenic bone scaffolds offer the same osteoconductive properties as autologous scaffolds. Allogenic scaffolds can be obtained from cadaveric samples, for example, from a tissue bank.

According to one embodiment, the osteoconductive scaffold includes a ceramic bone substitute. The ceramic bone substitute can be porous or non-porous. The term "porous" includes, but is not limited to, macroporosity (mean pore diameter greater than or equal to 100 um), mesoporosity (mean pore diameter less than 100 um but greater than or equal to 10 um) and microporosity (mean pore diameter less than 10 um). The pores may be of any size, shape or distribution, or within a predetermined tolerance. In addition, the pores can be interconnecting or non-interconnecting. In one embodiment, the diameter of the pores can range in size up to about 750 um. In another embodiment, the pore sizes rang up to about 500 um, with approximately 75% of the pores being at least 100 um in size and the remaining 25% of the pores being no more than 10 um in size.

In one embodiment, the ceramic bone substitute includes a calcium phosphate based compound. Suitable examples of calcium phosphates include amorphous calcium phosphate, crystalline calcium phosphate, or any combination thereof. For example, the calcium phosphate compound can be an apatite. Apatites are a group of calcium phosphate minerals, usually referring to hydroxyapatite $Ca_{10}(PO_4)_6(OH)_2$, fluoroapatite $Ca_{10}(PO_4)_6(F)_2$, chlorapatite $Ca_{10}(PO_4)_6(Cl)_2$ and bromapatite $Ca_{10}(PO_4)_6(Br)_2$ and can further include both silicate $(SiO_4^{4-})$ and carbonate $(CO_3^{2-})$ substituted hydroxyapatites, where the substitution is for one or more of the hydroxy and/or phosphate groups. In another embodiment, the ceramic bone substitute includes beta-tricalcium phosphate $Ca_3(PO_4)_2$, (b-TCP).

The osteoconductive scaffold can be of any shape as desired for the particular bone defect to be repaired. According to one embodiment the scaffold is a monolithic composition that can be either porous or non-porous. Suitable shapes can include, for example, spherical, cubic, wedge-shaped, oblong, cylindrical, or combinations thereof. In another embodiment, the osteoconductive scaffold can be a plurality of porous or non-porous granules. The specific surface area of the osteoconductive scaffold can vary. For example, when the scaffold is a porous granule, the specific surface area can range from about 0.1 $m^2/g$ to about 100 $m^2/g$.

The osteoconductive scaffold may be ceramic bone substitute particles or granules of any size or shape. The granules can be obtained by grinding or milling a calcium compound to a desired particle size or particle diameter. In one embodiment, the mean diameter of the granules range in size from about 0.05 mm to about 10 mm. In another embodiment, the mean diameter of the granules range in size from about 0.075 mm to about 5 mm. In another embodiment, the mean diameter of the granules range in size from about 0.075 mm to about 1 mm. In another embodiment, the mean diameter of the granules range in size from about 1.4 mm to about 2.8 mm. In another embodiment, the mean diameter of the granules range in size from about 2.8 mm to about 5.6 mm. In another embodiment, the mean diameter of the granules range in size from about 0.1 mm to about 0.750 mm According to another embodiment of the present disclosure, the osteoconductive scaffold can be further combined with a polymeric binder, such that the implant could be formed, for example into a moldable or pliable implant that could be shaped as desired to fit the area of the bone to be repaired.

The polymeric binder can include polymers such as homopolymers and copolymers (i.e., polymers including two or more different monomeric units), as well as polymer and copolymer blends, mixtures and combinations. The polymer can be a resorbable polymer, a non-resorbable polymer, or a combination thereof. In one embodiment, the polymeric binder includes a resorbable polymer, and the polymeric binder is substantially free of a non-resorbable polymer. According to one embodiment, the polymeric binder is resorbable in vivo and includes a resorbable polymer. The polymer(s) of the polymeric binder can also include a synthetic polymer, a non-synthetic polymer (i.e., a polymer obtained from a plant or animal), or a combination thereof.

Suitable polymers useful for preparing the polymeric binder include, but are not limited to, homopolymers or copolymers of monomers selected from L-lactide; L-lactic acid; D-lactide; D-lactic acid; glycolide; alpha-hydroxybutyric acid; alpha-hydroxyvaleric acid; alpha-hydroxyacetic acid; alpha-hydroxycaproic acid; alpha-hydroxyheptanoic acid; alpha-hydroxydecanoic acid; alpha-hydroxymyristic acid; alpha-hydroxyoctanoic acid; alpha-hydroxystearic acid; hydroxybutyrate; hydroxyvalerate; beta-propiolactide; beta-propiolactic acid; gamma-caprolactone; beta-caprolactone; epsilon-caprolactone; gamma-butyrolactone; pivalolactone; tetramethylglycolide; tetramethylglycolic acid; dimethylglycolic acid; trimethylene carbonate; dioxanone; those monomers that form liquid crystal polymers; those monomers that form cellulose; those monomers that form cellulose acetate; those monomers that form carboxymethylcellulose; those monomers that form hydroxypropylmethylcellulose; polyurethane precursors including macrodiols selected from polycaprolactone, poly(ethylene oxide), poly(ethylene glycol), poly(ethylene adipate), poly(butylene oxide), and a mixture thereof, isocyanate-functional compounds selected from hexamethylene diisocyanate, isophorone diisocyanate, cyclohexane diisocyanate, hydrogenated methylene diphenylene diisocyanate, and a mixture thereof, and chain extenders selected from ethylenediamine, 1,4-butanediol, 1,2-butanediol, 2-amino-1-butanol, thiodiethylene diol, 2-mercaptoethyl ether, 3-hexyne-2,5-diol, citric acid, and a mixture thereof, and any combination of two or more of the foregoing.

In one embodiment, the polymeric binder includes resorbable polymers. Suitable examples of resorbable polymers include, e.g., polymers derived from monomers selected from L-lactic acid, D-lactic acid, L-lactide, D-lactide, D,L-lactide, glycolide, a lactone, a lactam, epsilon-caprolactone, trimethylene carbonate, a cyclic carbonate, a cyclic ether, para-dioxanone, beta-hydroxybutyric acid, beta-hydroxypropionic acid, beta-hydroxyvaleric acid, saccharides, collagen, fibrin, albumin; and any combination of two or more of the foregoing.

In another embodiment, the polymeric binder includes a resorbable synthetic polymer. Non-limiting examples of resorbable synthetic polymers include, e.g., a poly(L-lactide) (co)polymer, a poly(D,L-lactide) (co)polymer, a polyglycolide (co)polymer, a polycaprolactone (co)polymer, a poly(tetramethylglycolic acid) (co)polymer, a polydioxanone (co)polymer, a polyhydroxybutyrate (co)polymer, a polyhydroxyvalerate (co)polymer, a poly(L-lactide-co-glycolide) copolymer, a poly(glycolide-co-trimethylene carbonate) copolymer, a poly(glycolide-co-caprolactone) copolymer, a poly(glycolide-co-dioxanone-co-trimethylene carbonate) copolymer, a poly(tetramethylglycolic acid-co-dioxanone-co-trimethylene carbonate) copolymer, a poly(glycolide-co-caprolactone-co-L-lactide-co-trimethylene carbonate) copolymer, a poly(lactide-co-caprolactone) copolymer, a poly(hydroxybutyrate-co-hydroxyvalerate) copolymer, a liquid crystal (co)polymer, a combination thereof, or a copolymer thereof.

According to an embodiment of the disclosure, where the osteoconductive scaffold is a ceramic bone substitute, such as apatite or b-TCP, suitable polymers for the polymeric binder can include, for example, polylactides, polyglycolides, cellulose based polymers, polylactones, and collagen based polymers, as well as, blends and copolymers thereof. According to another embodiment, the osteoconductive scaffold is a moldable implant that includes a plurality of porous b-TCP granules combined with poly-epsilon caprolactone as described in US Published Patent Appl. 2008/0003255, the disclosure of which is incorporated herein in its entirety. According to a further embodiment of the disclosure the osteoconductive scaffold is a pliable strip that includes a layer of porous b-TCP granules and a layer or layers of resorbable polymer as described in US Published Patent Appl. 2006/0008504, the disclosure of which is incorporated herein in its entirety. According to yet another embodiment, the osteoconductive scaffold is a moldable implant that includes a plurality of porous b-TCP granules combined with collagen that can be lyophilized into a rigid form prior to reconstitution by a fluid into a moldable form.

When the polymeric binder includes resorbable polymers, the osteoconductive scaffold containing them tend to exhibit complete in vivo or in vitro resorption from about 1 month to about 2.5 years, for example from about 2 months to about 2 years.

As previously described, the implant includes an osteoinductive small molecule. The osteoinductive small molecule can include compositions including corticosteroids, oxysterols, compounds that impact the HMG coA reductase pathway, and compounds that upregulate intracellular cAMP. Suitable examples of osteoinductive small molecules are given below in Table 1. According to one embodiment, suitable examples of osteoinductive small molecules include corticosteroids such as budesonide, fluticasone propionate, fluorometholone, halcinonide, clobetasol propionate, and blends and mixtures thereof.

The osteoinductive small molecule can further be combined with an excipient or excipients as desired. Pharmaceutically acceptable excipients are known in the art and include, for example, solvents and diluents (e.g., alcohols, propylene glycol, dimethylacetamide, DMSO, dimethyl isosorbide, methylpyrrolidone), solubilizers (Cremophors(R)), antioxidants (e.g., tocopherol (Vitamin E), ascorbic acid, methyl paraben, butylhydroxyanisole (BHA), butylhydroxytoluene (BHT), and propyl gallate), surfactants and emulsifiers (e.g., polysorbates (TWEEN 20, TWEEN 40, TWEEN 80), pluronics, labrasol), lipids (e.g., dimyristoylphophatidylcholine (DMPC), Dimyristoylphosphatidylglycerol (DMPG), distearoylphophatidylglycerol (DSPG), fillers (e.g., mannitol, polyvinylpyrrolidone), organic acids (e.g., citric acid, lactic acid, benzoic acid), hydrophilic polymers (e.g., polyethylene glycols (PEG 300, PEG 400), complexing agents (e.g., niacinamide, nicotinic acid, creatine, cyclodextrins), and preservatives (e.g., benzyl alcohol). According to one embodiment, the excipient can be selected from Captisol ® (sulfobutylether B-cyclodextrin, having the molecular formula $C_{42}H_{70}nO_{35}(C_4H_8SO_3Na)n$; where n = the average degree of substitution; CAS Number 182410-00-0), Cremphor EL ® (polvethoxylated castor oil, also known as Kolliphor® EL,; CAS Number 61791-12-6), DMA, DMSO, Labrasol ® (caprvlcaprovl macrogol glycerides), NMP, polyethylene glycol, propylene glycol, PVP, Solutol HS 15 ® (polyoxyl-15-hydroxystearate; also known as Kolliphor® HS 15; CAS Number 70142-34-6), Tween 20 ® (polyethylene glycol sorbitan monolaurate; CAS Number 9005-64-5), Tween 80 ® (polyethylene glycol sorbitan monooleate; CAS Number 9005-65-6), and mixtures and derivatives thereof.

The osteoinductive small molecule, according to the present disclosure can be combined with the scaffold pre-operatively as well as intra-operatively. Where the osteoinductive small molecule is combined pre-operatively, it can be combined with the scaffold as part of a manufacturing process where the small molecule could be applied to the scaffold in a buffered solution and then subsequently lyophilized or air dried. The small molecule may also be applied by spray drying or other coating methods. The implant could then be subsequently packaged and sterilized. Where the osteoinductive small molecule is combined intra-operatively with the scaffold, the scaffold can be dipped or coated with a buffered solution including the osteoinductive small molecule and then applied to the bone site to be repaired.

According to another embodiment of the disclosure, the implant can further include an osteogenic material to provide a viable cell population to the bone repair site. The osteogenic material can be obtained from both autogenic sources as well as allogenic sources, such as cadaveric sources or tissue banks Suitable osteogenic material can include, for example, viable cell sources such as stem cells, multipotent cells, pluripotent cells, osteoprogenitor cells, pre-osteoblasts, mature osteoblasts, and blends and mixtures thereof. According to one embodiment the osteogenic material is obtained from autogenic and/or allogenic human bone marrow, and according to another embodiment, the osteogenic material is obtained from autogenic and/or allogenic human lipoaspirate. Both the bone marrow and lipoaspirate can be processed to further enhance the desired cell population for example by filtration, separation and/or concentration. In order to preserve the viability of the cell population of the osteogenic material, the osteogenic material is typically combined with the osteoconductive scaffold and osteoinductive material at or near the time of the implantation procedure.

Figure 10:
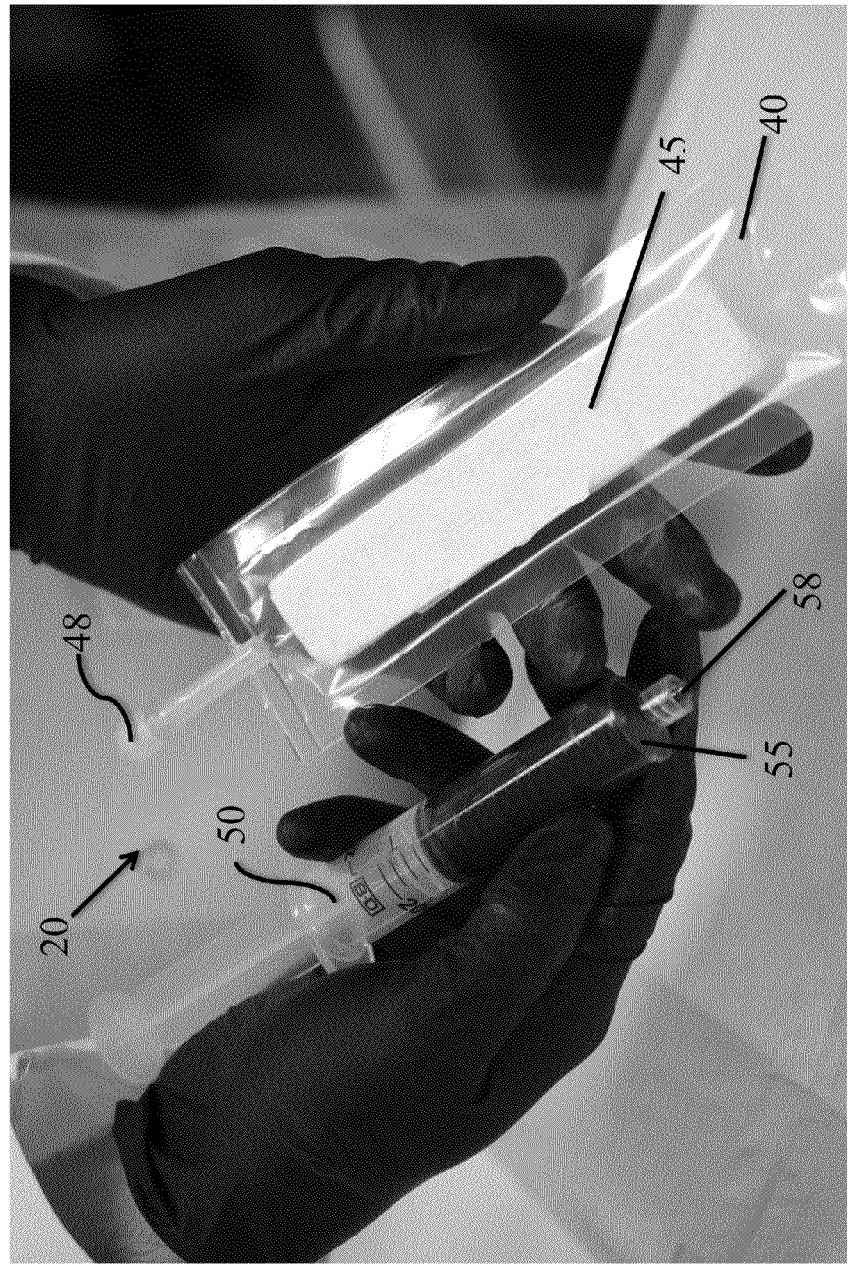
FIG. 10 is an implant system having a first container housing an osteoconductive scaffold including a polymeric binder and a second container housing an osteogenic material according to one embodiment.
Figure 11:
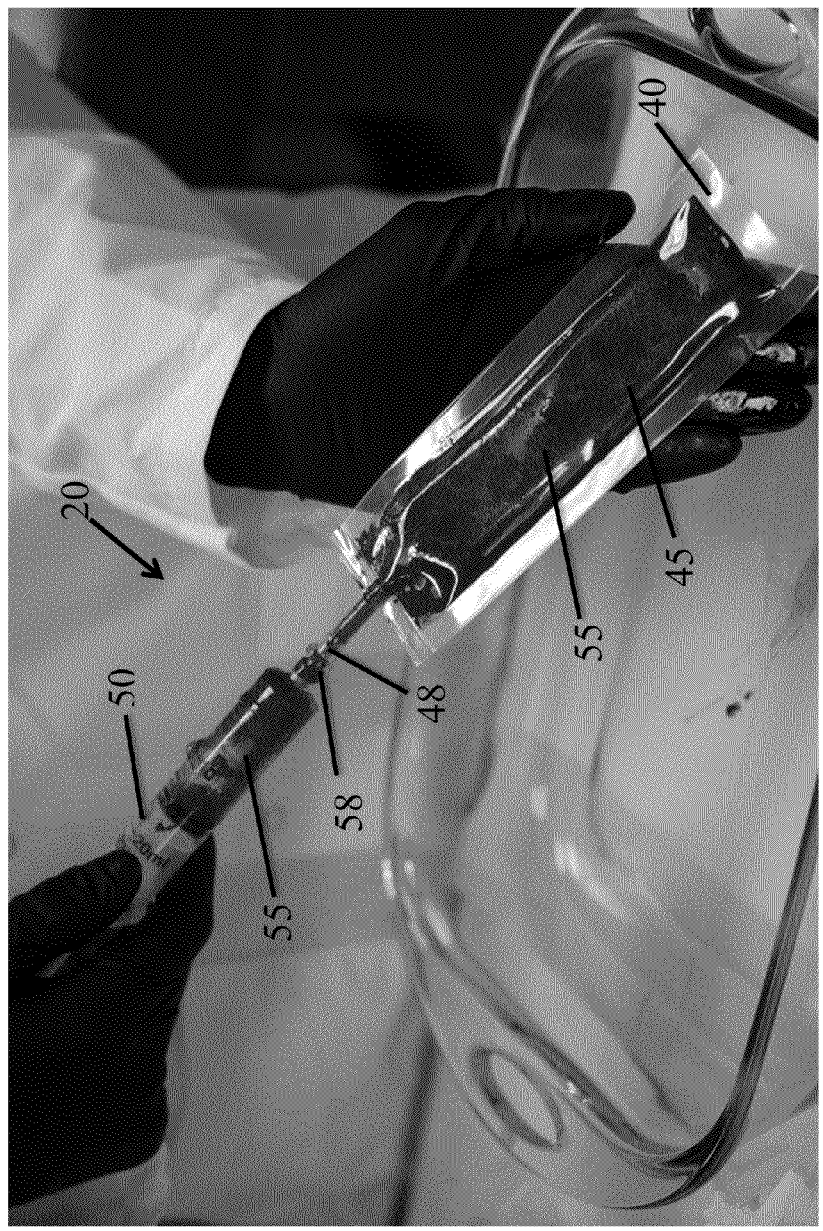
FIG. 11 is the implant system of FIG. 10 where the second container is connected to the first container to transfer the osteogenic material from the second container to the first container.
Figure 12:
FIG. 12 is an implant formed according to the implant system as shown and described in FIGS. 10 and 11.

Referring to FIGS. 10-12, a system 20 for forming an implant 30, includes an osteoconductive scaffold 45 housed in a first sterile container 40 having an opening 48 and an osteogenic material 55 housed in a second sterile container 50 having an opening 58. The second container opening 58 is adapted to connect with the first container opening 48 such that the osteogenic material 55 can be transferred from the second container 50 to the first container 40 via the connection of the first opening 48 and the second opening 58. The system 20 includes an osteoinductive small molecule that can be in the first container 40 and that can already have been incorporated with the scaffold 45 in a manner such as has been previously described. The osteoinductive small molecule can also be included with the osteogenic material 55 in the second container 50. The osteoinductive small molecule can also be combined with the scaffold 45 after the osteogenic material 55 has been transferred to the first container 45 and incorporated with the scaffold 45. The osteoinductive small molecule can also be housed in a third container (not shown) having an opening that is adapted to connect with the first container opening such that the osteoinductive small molecule can be transferred from the third container into the first container and combine with the scaffold.

The scaffold 45 can further include a polymeric binder that gives the implant 30 moldabilty and/or pliability depending upon the desired polymer or polymers selected. A moldable implant 30 formed from the system 20 is shown in FIG. 12 including a scaffold 45 of b-TCP porous granules and collagen polymer, having a dried osteoinductive small molecule adsorbed on its surface and an osteogenic material 55 of autologous bone marrow aspirate. Alternatively, the osteoinductive small molecule can combined with the scaffold 45 intra-operatively either prior to or after transfer of the osteogenic material 55 to the scaffold 45. The implant 30 is moldable upon infusion of the osteogenic material 55 with the scaffold 45.

EXAMPLES

Example 1

In Vitro Candidate Screening and Exposure Profile Analysis

Samples from several classes of small molecule compounds including, corticosteroids, glucocorticoids, oxysterols, compounds that impact the HMG coA reductase pathway and compounds that upregulate intracellular cAMP were screened for osteoinductive potential with an alkaline phosphatase (ALP) assay in primary human mesenchymal stem cells (MSCs). Sample compounds were screened over a dose range in a multiwell plate format using DNA to normalize the ALP response as a function of cell number. These dose response curves allowed for the determination of an EC50 to measure relative potency of the osteogenic response between compounds. FIG. 1 is a representative dose response curve for two of the corticosteroid compounds tested, clobetasol propionate and dexamethasone. In addition to the functional analysis, certain identified compounds were run through an in vitro L929 cytotoxicity assay to determine a CC50. Thus, compounds were evaluated first for their potency and subsequently for cytotoxicity, shown below in Table 1.

TABLE 1

| | OI Assay (ALP) EC50 (nM) | Cytotox (CTG) CC50 (uM) |
|---|---|---|
| Oxysterols | | |
| 22(S)-hydroxy-cholesterol | >12000 | |
| 22(r)-hydroxy-cholesterol | 785 | >12 |
| 20a-hydroxy-cholesterol | >12000 | >12 |
| 25-hydroxy-cholestero | >12000 | |
| 19-hydroxy-cholesterol | >12000 | |
| Steroids | | |
| Betamethasone | 1.96 | |
| Fludrocotisone actetate | 4.12 | |
| Budesonide | 0.296 | >30 |
| Fluticasone propionate | 0.0065 | >1 |
| Dexamethasone | 0.95 | >50 |
| Fluorometholone | 0.319 | >5 |
| Halcinonide | 0.235 | >10 |
| Flurandrenolide | 1.56 | |
| Clobetasol propionate | 0.012 | >30 |
| Diflorasone Diacetate | 1.38 | |
| Triamcinolone | 4.13 | |
| Aldosterone 98% | 287 | |
| Deflazacort | 9.85 | |
| Intracellular cAMP Upregulators | | |
| Pentoxifylline (Trental) | >10000 | |
| Dipyridamole | 306 | >30 |
| Dipyridamole | >10000 | |
| 3-isobutyl 1-methylxanthine (IBMX) | >10000 | |
| Propentofylline | >10000 | |
| dbcAMP | >10000 | |
| HMG Co-A Reductase Modulators | | |
| Zaragozic Acid A | 715 | >30 |
| β-Sitosterol | >12000 | |
| bm15766 sulfate | >10000 | |
| Triparanol | >10000 | |
| Fosmidomycin | >10000 | |
| GGTI-286 | >12000 | |
| Patulin | >10000 | |
| FTI-277 trifluoroacetate salt | >12000 | |

Example 2

Relative Potency

One part of this technology may involve coating an osteoconductive scaffold with an osteoinductive small molecule compound to thereby deliver the compound locally when the scaffold is implanted. Consequently, the optimal time and concentration profile required for the compound to remain at the site in order to influence an osteogenic outcome was determined. Initially, potency was determined by looking at exposure over 6 days. In order to better understand the optimal exposure profile, MSCs were treated over a series of dose ranges for exposure times starting at 1 hour out to 4 days, after which the compound treated media was removed and the cells were allowed to continue to assay completion under basal media conditions. This allowed for the determination of the relative potency of the compounds over short exposure periods and gave an indication of the release requirements that would be necessary to achieve the desired osteogenic outcome.

Figure 2:
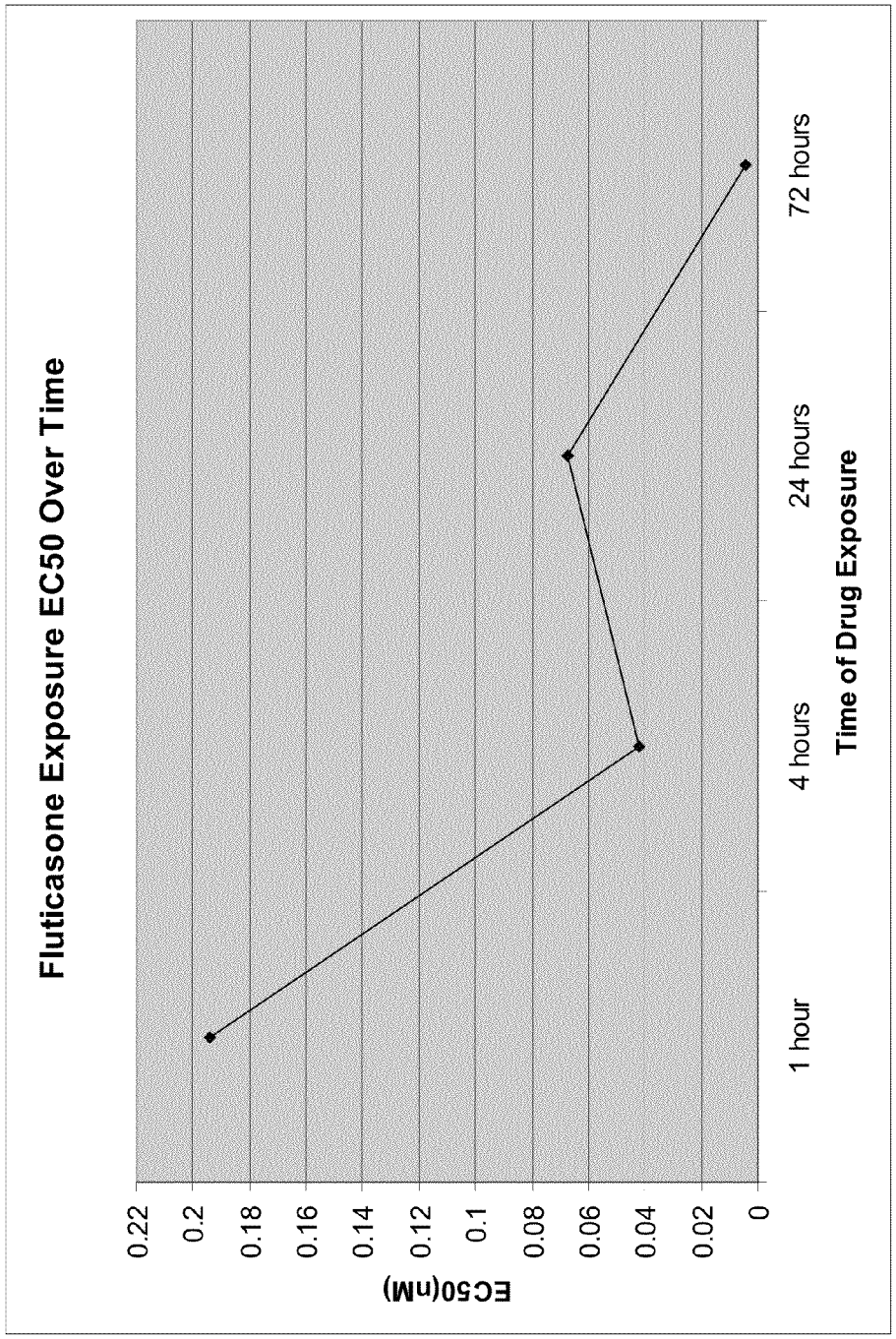
FIG. 2 is a graphical representation of the relative potency of a small molecule according to another embodiment.

Table 2 below, list the relative potency results of selected compounds that were tested over a specific timeframe of 1 hr., 4 hr., 24 hr., and 72 hr., as well as the time range for the selected compounds to reach the full response of the ALP assay control (dexamethasone at 10 nM for 6 days). FIG. 2 is a representative relative potency graph of a corticosteroid, fluticasone propionate, based on the results shown in Table 2.

TABLE 2

| Compound | EC50(nM) 6 days | EC50(nM) 1 hr. | EC50(nM) 4 hr. | EC50(nM) 24 hr. | EC50(nM) 72 hr | Max Osteogenic Response |
|---|---|---|---|---|---|---|
| Fluticasone | 0.0065 | 0.194 | 0.0422 | 0.0676 | 0.0042 | 48-72 hrs. |
| Clobetasol | 0.012 | 0.0605 | 0.019 | 0.0804 | 0.00371 | 72 hrs. |
| Halcinonide | 0.235 | 2.29 | — | 1.26 | 0.115 | 72 hrs. |
| Budesonide | 0.296 | 47.9 | 5.47 | 4.48 | 0.0533 | 72 hrs. |
| Fluoromethalone | 0.319 | NC | 0.464 | NC | 0.146 | 144 hrs. |
| Dexamethasone | 0.95 | NC | 0.787 | NC | 0.277 | — |

NC: Not Calculated
—: Not Determined

Example 3

In Vitro Release Kinetics

Figure 3A:
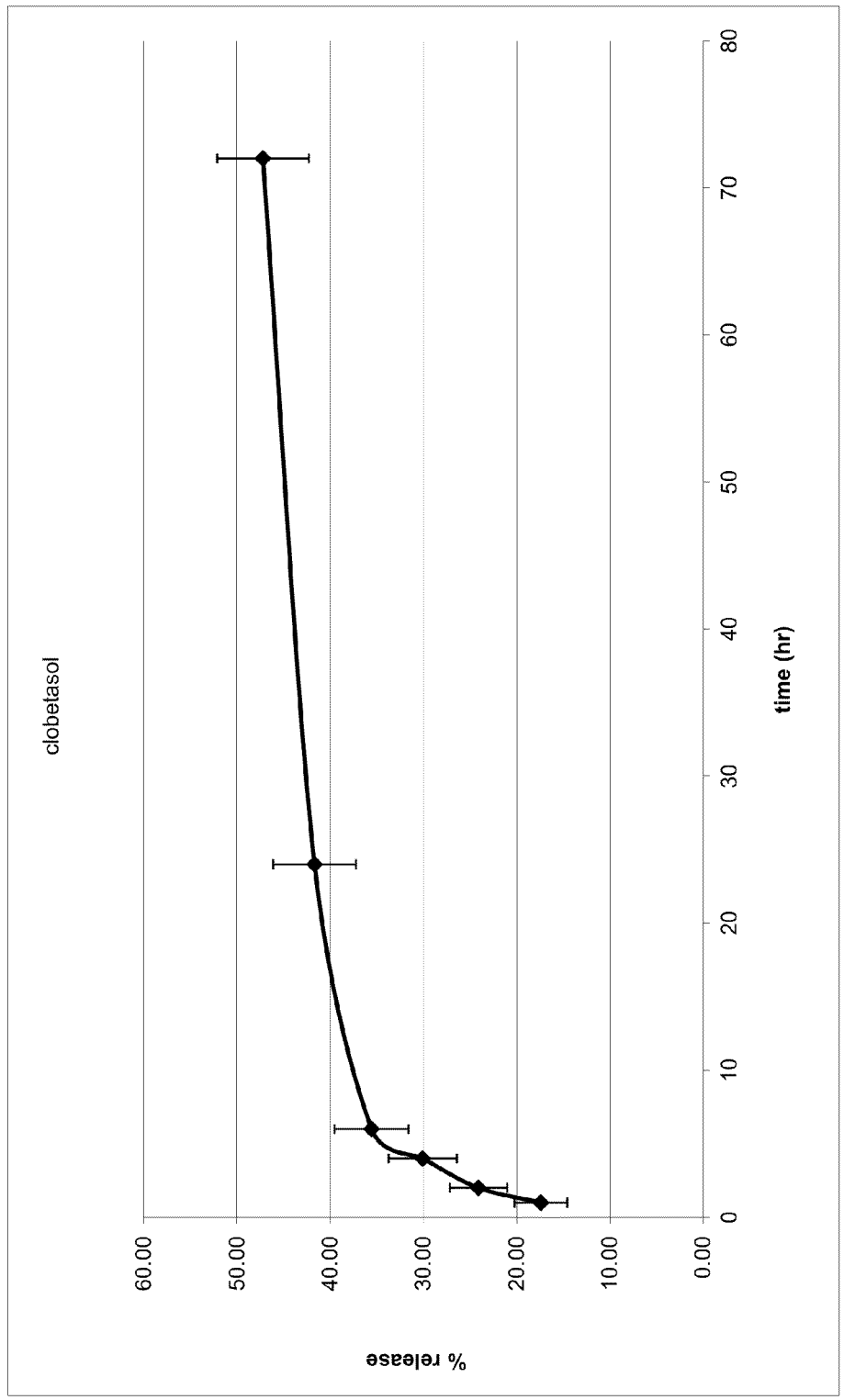
FIGS. 3A-3C are graphical representations of in vitro time release of several small molecules from an osteoconductive scaffold measured using LC/MS according to one embodiment.
Figure 3B:
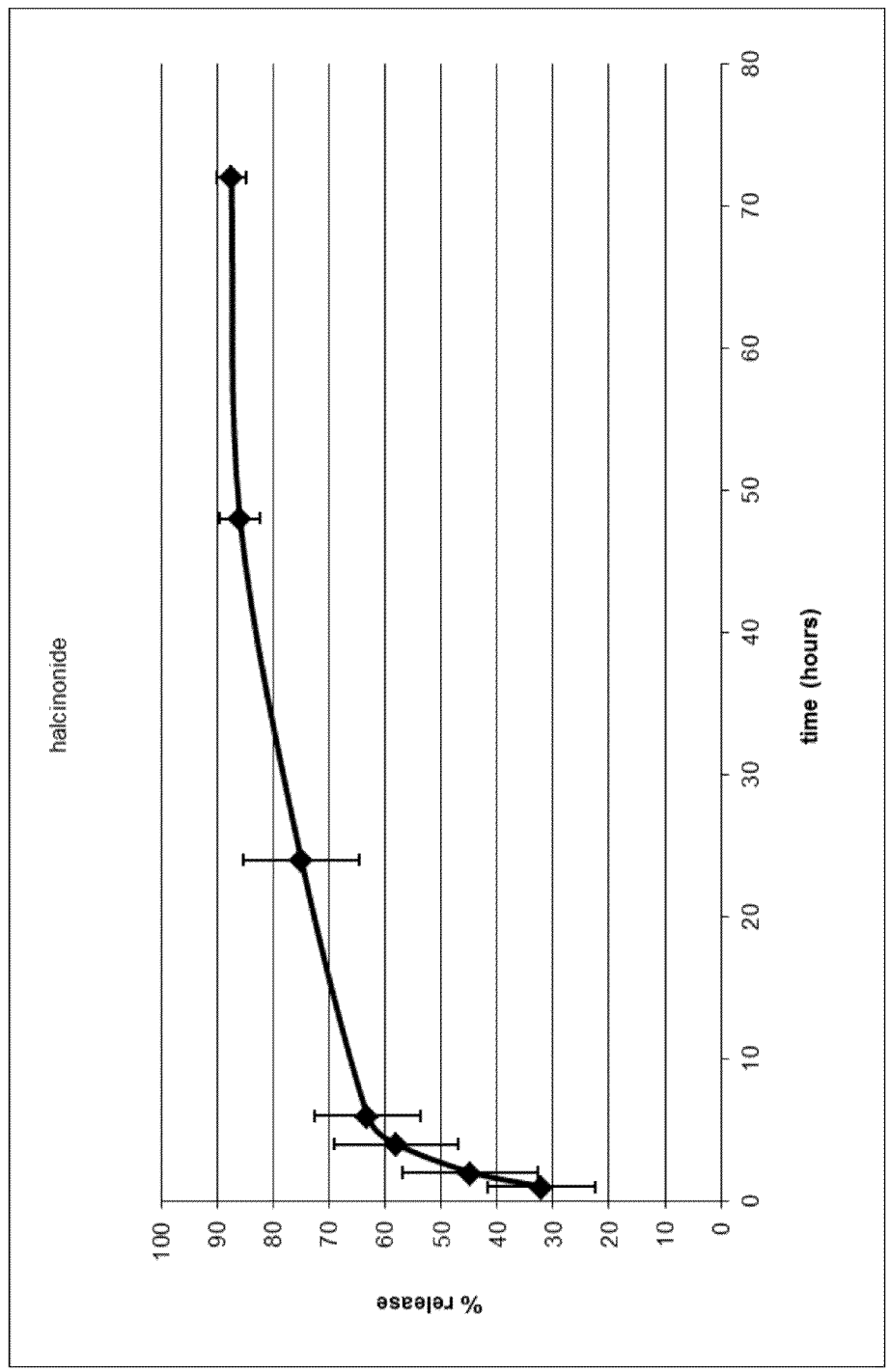
Figure 3C:
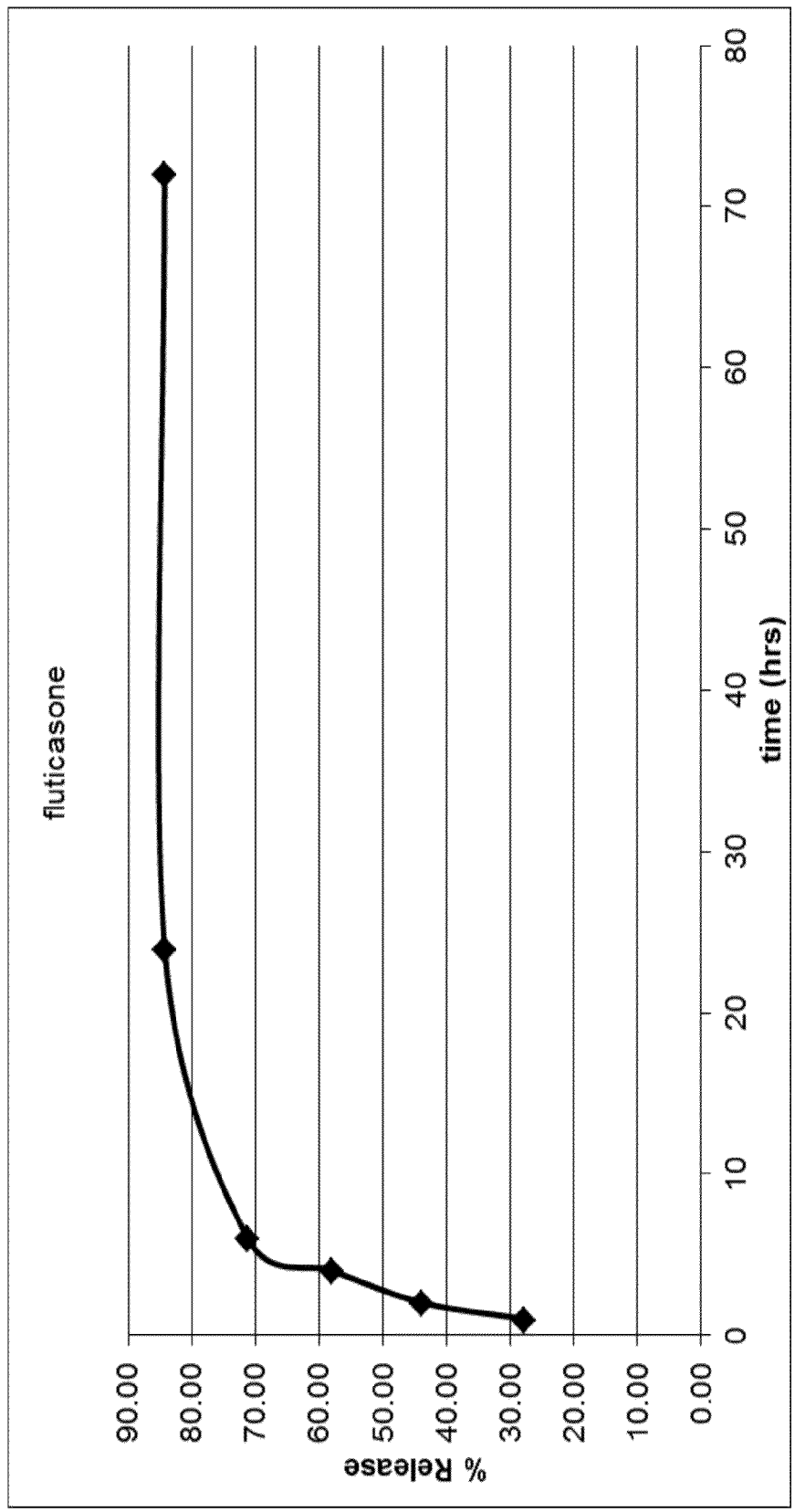
Figure 4:
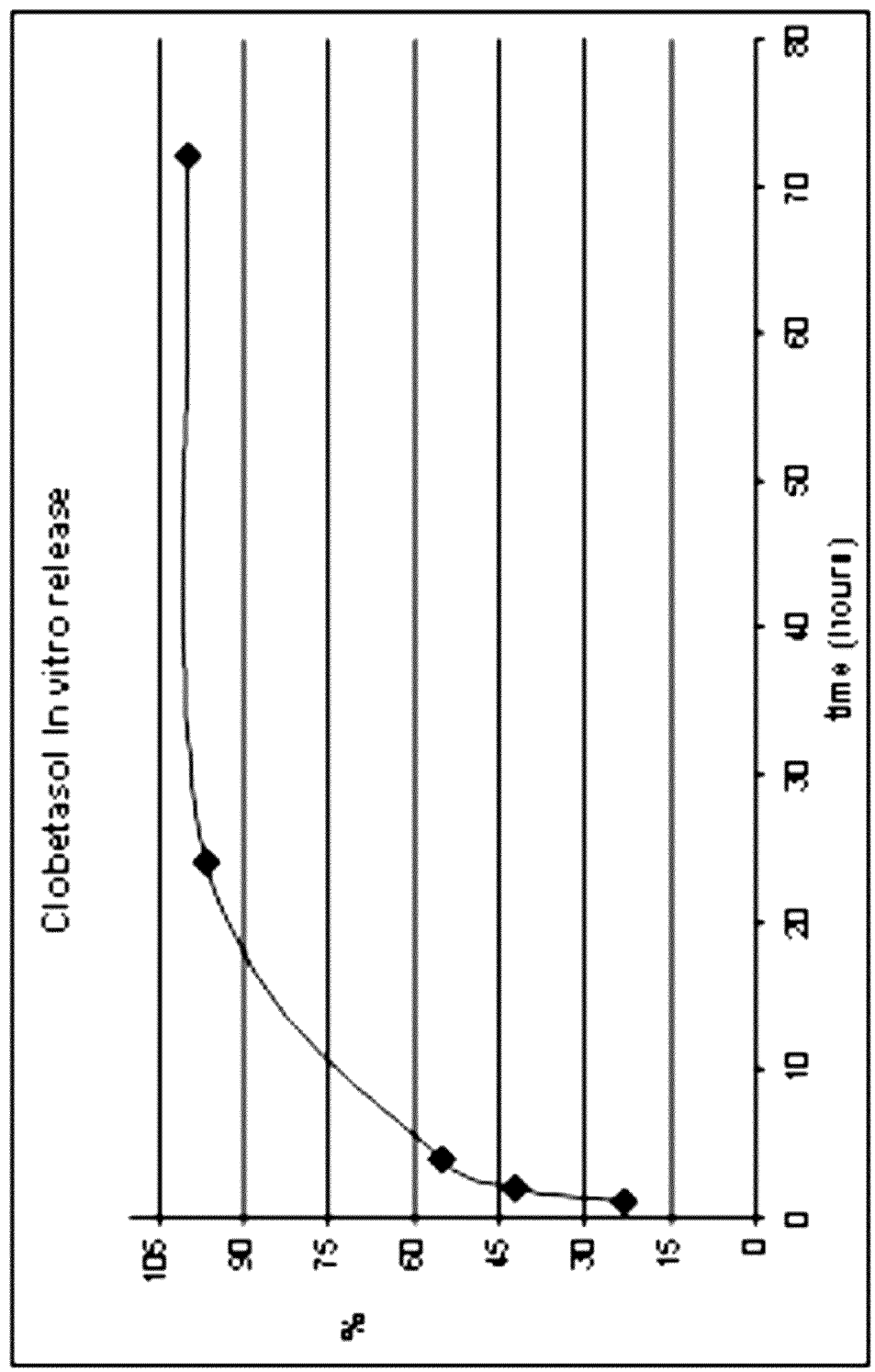
FIG. 4 is a graphical representation of in vitro time release of a small molecule from another osteoconductive scaffold measured using radiolabeling according to another embodiment.

For selected small molecule compounds identified in Table 1, the solubility was determined in a coating solution (ethanol) and in an aqueous release media. The small molecule compound was dissolved in ethanol and added to a scaffold at its maximum ethanol solubility and allowed to air dry. Scaffold I was made of porous b-TCP granules and a resorbable poly(lactide-co-e-caprolactone) in the form of a pliable strip (ChronOS Strip, Product No.: 07.801.100.99S, commercially available from Synthes Spine, West Chester, Pa.). Scaffold II was made of a porous b-TCP granules and a collagen polymer that had been lyophilized into a rigid mass. The scaffolds coated with the small molecule compound were placed in cell culture media under conditions where the concentration of the small molecule would be below its solubility even if all of the molecule was released (sink conditions) and the small molecule compound release was monitored via liquid chromatography-mass spectrometry (LC/MS) or by measuring radiolabeled content. This analysis was able to provide a cumulative percent release of the small molecule compound from the scaffold over time. FIG. 3A-3C are graphical illustrations of in vitro time release profiles from Scaffold I for the small molecules clobetasol propionate, halcinonide, and fluticasone propionate, respectively, measured using LC/MS. FIG. 4 is a graphical illustration of an in vitro time release profile for the small molecule clobetasol propionate from Scaffold II measured using radiolabeled content.

Example 4

Bioassay

Figure 5:
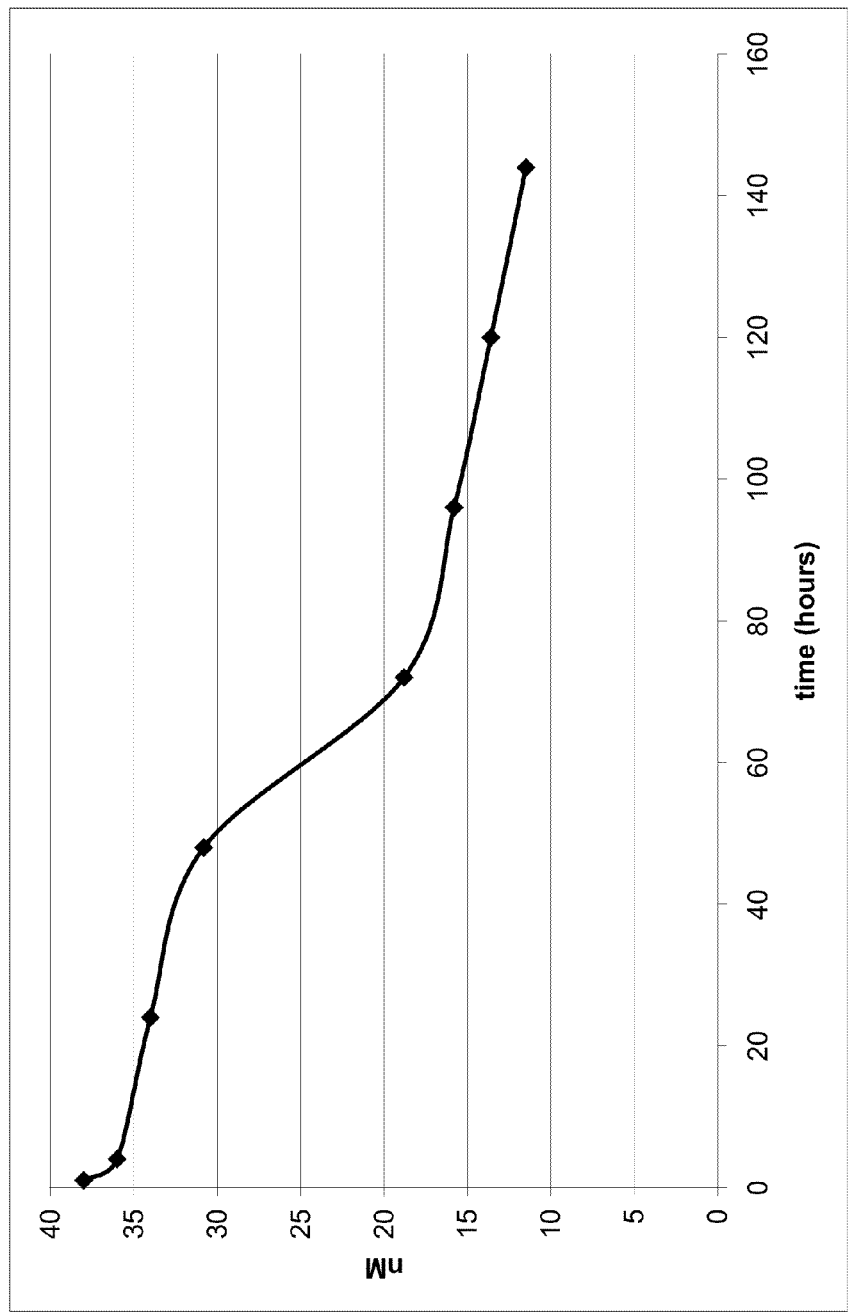
FIG. 5 is a graphical representation of a theoretical in vivo release profile for a small molecule from an osteoconductive scaffold according to another embodiment.
Figure 6:
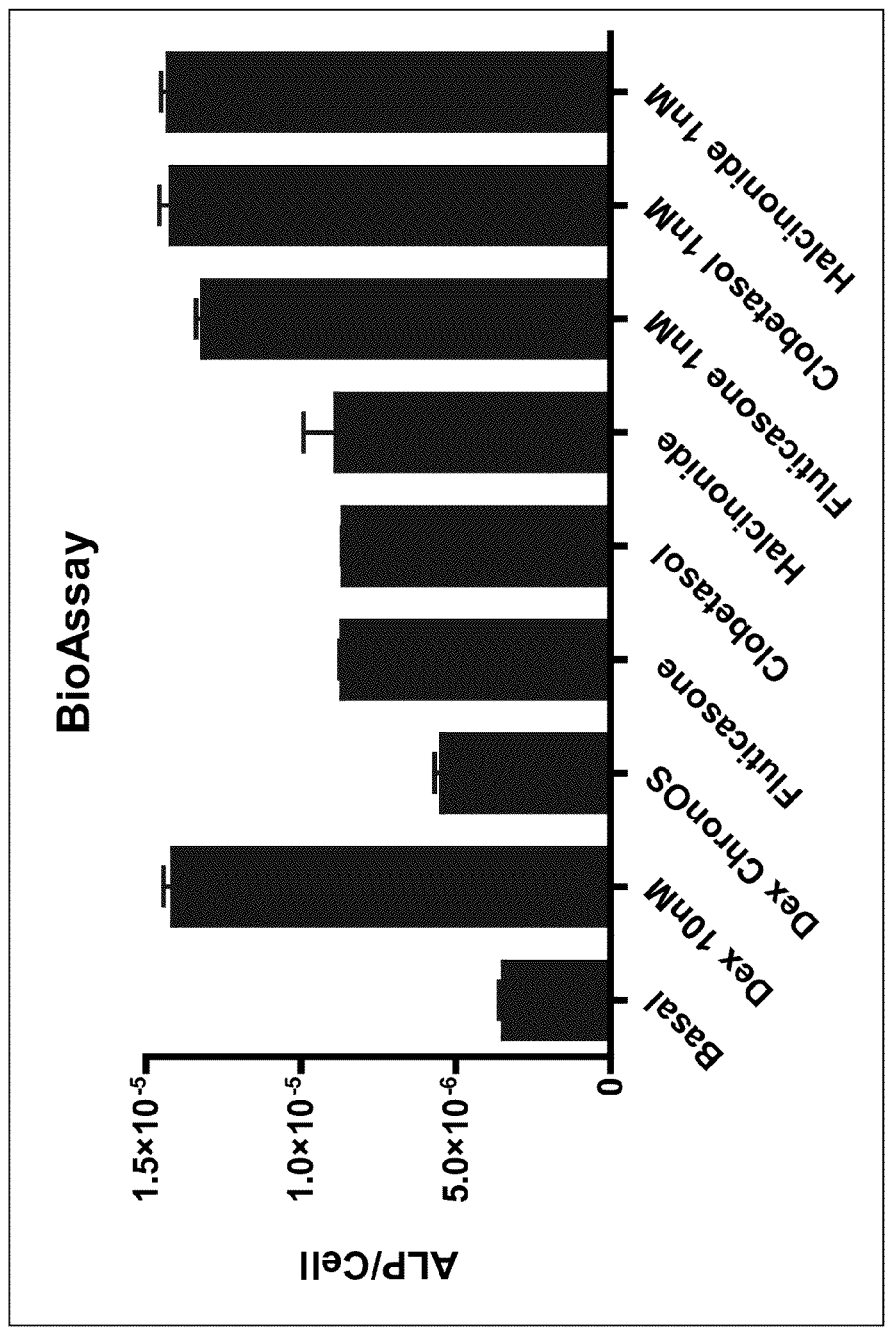
FIG. 6 is a graphical representation of measured osteoinductivity of several small molecules as measured on an osteogenic material in an ALP assay according to embodiments of the present disclosure.

Once the required exposure profile and corresponding release kinetics were identified, these two data sets were analyzed and combined to determine if the time-concentration profile of a selected small molecule compound released directly off of Scaffold I had the potential to elicit the same osteoinductive outcome in an osteogenic material (MSCs) as the same small molecule compound in solution. Coating concentrations were determined based on the aforementioned exposure and release profile data. FIG. 5 is a graphical illustration of a theoretical concentration exposure of a released small molecule compound from Scaffold I as determined from the previously mentioned data sets. Selected small molecule compounds were coated onto Scaffold I and allowed to release into cell culture media. At each selected time point specified in FIG. 5, the media was removed and replaced with fresh media. The removed media was transferred to MSCs in culture and the MSCs were exposed to that media until the next time point, at which time the media was removed from the MSCs and the process repeated with the media removed from Scaffold I at that timepoint. After the full six day experiment the MSC were analyzed with the ALP assay. The results from this experiment demonstrated that all of the small molecule compounds that were tested had adsorbed onto and released from the scaffold, that the small molecule compounds were osteoinductive, and that they were released at a concentration profile sufficient to elicit an osteogenic response shown from the MSC cell population that they contacted. FIG. 6 is a graphical illustration of the ALP assay results showing that each small molecule compound tested elicited an osteogenic response greater than the basal level.

Example 5

In Vitro 3-D Efficacy

Figure 7:
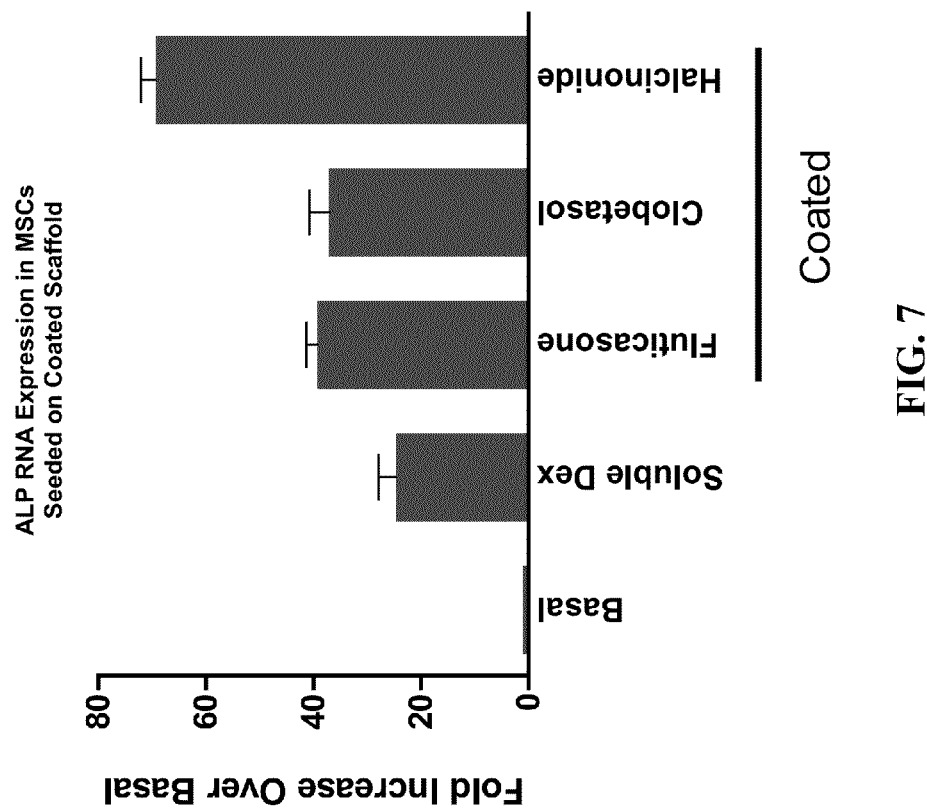
FIG. 7 is a graphical representation showing the amount of ALP RNA expression in osteogenic material seeded onto an osteoconductive scaffold coated with selected osteoinductive small molecules according to embodiments of the present disclosure.

The osteoinductive potential of selected small molecule compounds were determined in vitro by seeding MSCs onto a three dimensional b-TCP polymer composite scaffold, Scaffold I, which had been coated with selected compounds prior to seeding. These cells were allowed to culture for a period of time after which they were assayed for alkaline phosphatase (ALP) RNA content, an early marker of osteogenic differentiation. FIG. 7 is a graphical illustration showing the amount of ALP RNA expression in the MSCs, expressed as a fold increase over basal conditions (standard culture conditions). In this example, dexamethasone (a control for the assay) was added to the culture media in solution whereas in all other cases the compounds were precoated on to Scaffold I followed by addition of the MSCs. The cells were then cultured for three days and assayed for their level of osteogenic response via ALP RNA expression. Fluticasone, clobetasol and halcinonide all upregulated osteogenic differentiation of MSCs significantly.

Example 6

In Vivo Release Analytics

Figure 8:
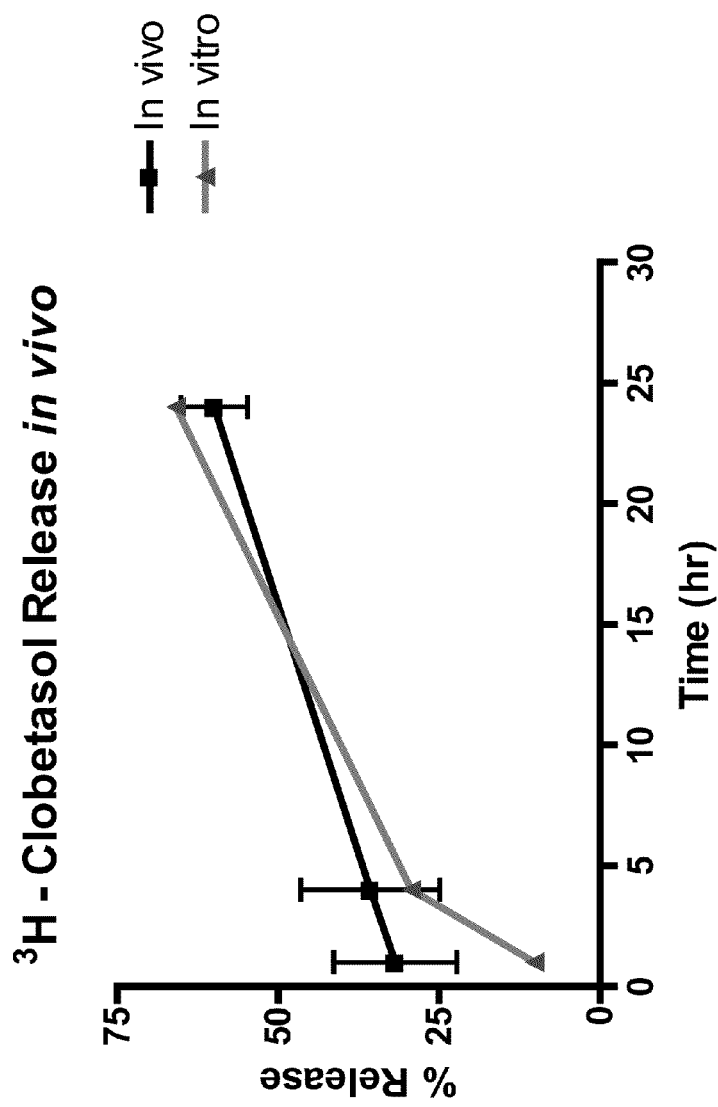
FIG. 8 is a graphical representation of the release profile of an osteoinductive small molecule in vitro and the release profile of the same osteoinductive small molecule that has been radiolabeled and released in vivo from an osteoconductive scaffold according to embodiments of the present disclosure.

Compared to an in vitro setting the in vivo environment is more complicated and may include an inflammatory response, a limited blood supply, and a transient cell population. Consequently, it is critical to verify the applicability of the in vitro data to an in vivo environment. In order to do this Scaffold I was separately coated with two compounds, 20S- hydroxycholesterol and 3H-clobetasol propionate (radiolabeled), and implanted in a rabbit radial bone defect model. The surrounding muscle tissue and scaffold were separately explanted at 1, 4, and 24 hours post implantation and assayed for drug content. FIG. 8 is a graphical illustration of the in vivo release profile of clobetasol propionate plotted together with the previously measured in vitro release profile.

Example 7

In Vivo Study

An evaluation of two small molecule compounds, dexamethasone and 20S-hydroxycholesterol, was performed in the rabbit radial defect model. Scaffold I was coated with the compounds intraoperatively, combined with autogenic bone marrow, and implanted in a 15 mm radial defect. Radiographs were taken at 3 and 6 weeks post-operatively, after which the animals were sacrificed and explants analyzed by micro CT. At three weeks post op the radiographs for 20S-hydroxycholesterol appeared to have an enhanced periosteal response but at 6 weeks there were no statistically significant different between the samples radiographically.

Example 8

Mineralization Assay

An assay was conducted to measure the differentiation-inducing potential of clobetasol by examining the production of hydroxyapatite (HA) in MSCs and osteoblasts. Frozen MSCs and Osteoblasts (Lonza) were thawed and grown to 80% confluence, then plated at passage 5-7 (for MSCs) and 2-10 (osteoblasts) into 96 well plates at approximately 8000 cells/well and allowed to set overnight. Media were completely aspirated off of all of the plates. Designated wells were replaced with 150uL of one of the following:

Basal—(MSC/7.5mM β-glycerophosphate (BGP) & Ascorbic acid) or (osteoblasts/7.5mM BGP);
Mineralization Control—(osteoblasts/7.5mM BGP & 400nM Hydrocortisone) or (MSC/7.5mM BGP, 100 nM Dexamethasone & Ascorbic acid); or
Clobetasol Test Agent—(osteoblasts/7.5 mM BGP+clobetasol), or (MSC/7.5 mM BGP, Ascorbic acid+clobetasol).

Clobetasol was tested at the following concentrations: 0.03nM, 0.1nM, 0.3nM, 1nM, 3nM, and 10nM. All media was replaced every 3-4 days until Day 14 was reached.

Figure 9:
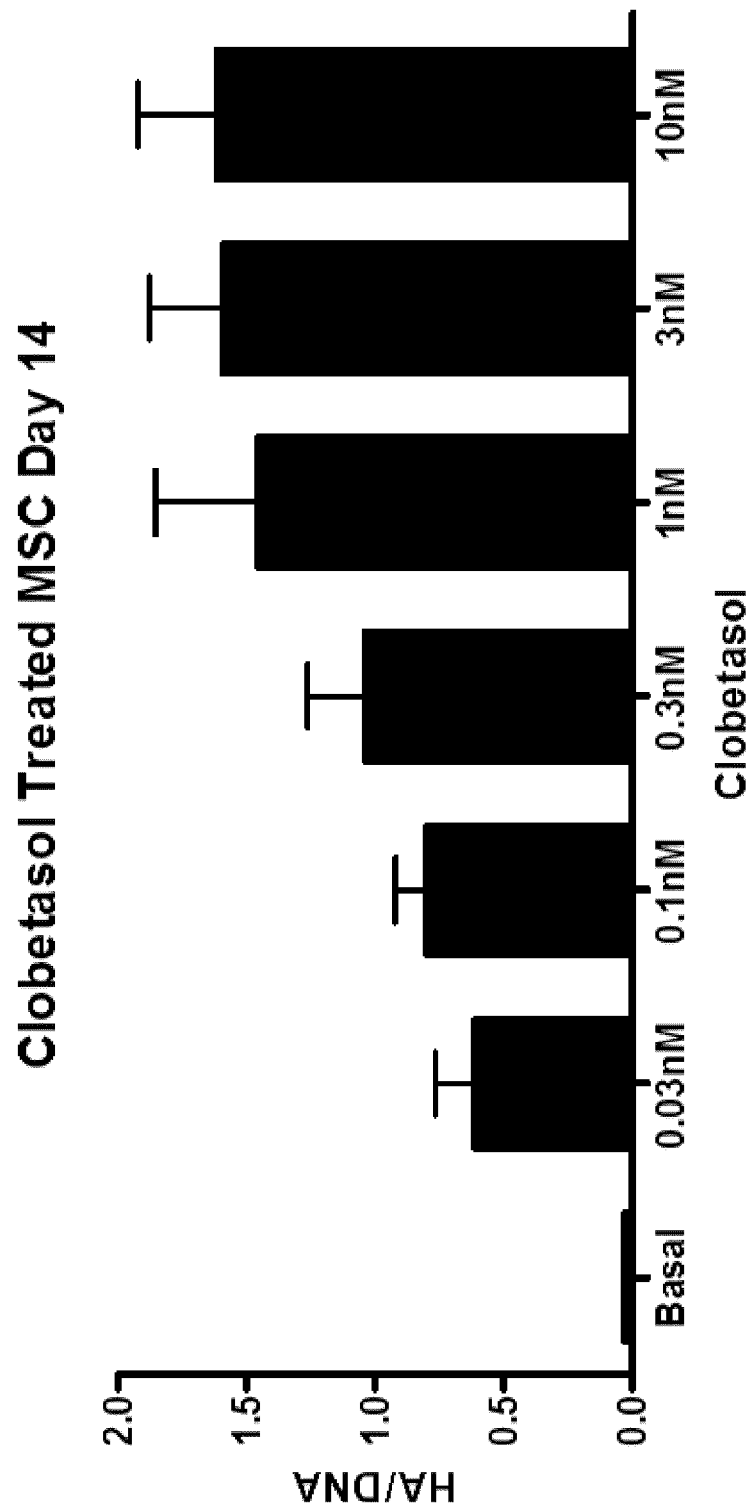
FIG. 9 is a graphical representation showing the differentiation potential of an osteoinductive small molecule reflecting the production of hydroxyapatite (HA) expression in osteogenic material, according to embodiments of the present disclosure.

Post treatment analysis was conducted using an OsteoImage Kit (Lonza) and Hoechst Stain/Extraction. HA data was generated using the OsteoImage Assay protocol and DNA data was generated using the Hoechst Assay. HA/DNA values were generated from the data analysis and were graphically plotted as shown in FIG. 9.

Example 9

Excipient Testing at Variable pH Levels

The goal of these experiments was to increase the solubility of the compound such that increased doses could be added to material scaffolds. In a set of experiments, the solubility of clobetasol propionate and fluticasone propionate were evaluated at three distinct pH levels with a series of excipients. Phosphate buffered solutions were prepared at pH levels 3 (Low), and 7 (Medium), and a Tris buffered solution was prepared at pH level 9 (High). Solubility of the compound in the presence of a given excipient was measured at the individual pH levels as a fold increase over the solubility of the compound with no excipient present. Data regarding the solubility of clobetasol propionate in combination with the excipients is given below in Table 3. Data regarding the solubility of fluticasone propionate in combination with the excipients is given below in Table 4.

TABLE 3

(Clobetasol Propionate)

| Excipient | pH (Low) | pH (Med) | pH (High) |
|---|---|---|---|
| Captisol | 56.19 | 48.78 | 22.45 |
| Cremophor_EL | 2.40 | 5.00 | 2.30 |
| Dimethyl_isosorbide | 24.82 | 26.92 | 27.03 |
| DMA | 4.10 | 2.31 | 4.92 |
| DMSO | 1.88 | 1.41 | 2.77 |
| Labrasol | 3.17 | 0.44 | 0.85 |
| NMP | 6.39 | 5.87 | 6.01 |
| PEG400 | 18.51 | 17.75 | 22.58 |
| Propylene_glycol | 35.43 | 24.24 | 25.65 |
| PVP | 7.71 | 3.93 | 8.46 |
| Solutol_HS_15 | 13.11 | 6.96 | 6.42 |
| Tweens | 32.52 | 19.94 | 23.32 |

TABLE 4

(Fluticasone Propionate)

| Excipient | pH (Low) | pH (Med) | pH (High) |
|---|---|---|---|
| Captisol | 55.01 | 80.81 | 67.60 |
| Cremophor_EL | 94.00 | 138.82 | 89.92 |
| Dimethyl_isosorbide | 4.14 | 5.78 | 5.01 |
| DMA | 6.67 | 8.41 | 7.07 |
| DMSO | 1.79 | 1.96 | 1.84 |
| Labrasol | 54.03 | 85.96 | 79.23 |
| NMP | 6.39 | 9.02 | 7.96 |
| PEG400 | 3.22 | 4.32 | 3.55 |
| Propylene_glycol | 5.63 | 7.89 | 5.90 |
| PVP | 2.21 | 3.98 | 2.73 |
| Solutol_HS_15 | 3.82 | 5.00 | 4.47 |
| Tweens | 194.37 | 272.98 | 231.06 |

Although the present disclosure has been described in accordance with several embodiments, it should be understood that various changes, substitutions, and alterations can be made herein without departing from the spirit and scope of the present disclosure, for instance as indicated by the appended claims. Thus, it should be appreciated that the scope of the present disclosure is not intended to be limited to the particular embodiments of the process, manufacture, and composition of matter, methods and steps described herein. For instance, the various features as described above in accordance with one embodiment can be incorporated into the other embodiments unless indicated otherwise. Furthermore, as one of ordinary skill in the art will readily appreciate from the present disclosure, processes, manufacture, composition of matter, methods, or steps, presently existing or later to be developed that perform substantially the same function or achieve substantially the same result as the corresponding embodiments described herein may be utilized according to the present disclosure.

It will be appreciated by those skilled in the art that various modifications and alterations of the invention can be made without departing from the broad scope of the appended claims. Some of these have been discussed above and others will be apparent to those skilled in the art.

The invention claimed is:

1. A method of inducing bone growth in a patient in need thereof, comprising implanting in the patient an implant comprising:
an osteoconductive scaffold; and, an osteoinductive small molecule selected from fluticasone propionate and clobetasol propionate and blends and mixtures thereof;

wherein the scaffold is selected from the group consisting of autograft material, allograft material, ceramic bone substitute, and blends and mixtures thereof; and, wherein the osteoinductive small molecule is solubilized in an excipient selected from the group consisting of Captisol, Cremphor EL, DMA, DMSO, Labrasol, NMP, polyethylene glycol, propylene glycol, PVP, Solutol HS 15, Tween 20, Tween 80, and mixtures thereof.

2. The method according to claim 1, wherein the implant further comprises an osteogenic material.

3. The method according to claim 2, wherein the osteogenic material is derived from the group consisting of autogenic bone marrow aspirate, autogenic lipoaspirate, allogenic bone marrow aspirate, allogenic lipoaspirate, and blends and mixtures thereof.

4. The method according to claim 1, wherein the scaffold comprises a ceramic bone substitute that is a calcium-phosphate based compound selected from the group consisting of apatites and tricalcium phosphates, and blends and mixtures thereof.

5. The method according to claim 4, wherein the ceramic bone substitute comprises a plurality of porous granules having an average granule diameter of about 0.5 mm to about 4.0 mm and an average pore diameter of about 20 82 m to about 500 μm.

6. The method according to claim 1, wherein the scaffold further includes a polymeric binder.

7. The method according to claim 6, wherein the polymeric binder is selected from the group consisting of polylactides, polyglycolides, polycaprolactones, collagen, cellulose, and copolymers, blends and mixtures thereof.

8. The method according to claim 1, wherein the step of implanting the implant comprises:
   (a) implanting the osteoconductive scaffold; and
   (b) implanting the osteoinductive small molecule.

9. The method according to claim 8, wherein steps (a) and (b) occur simultaneously.

10. The method according to claim 8, wherein steps (a) and (b) occur separately.

11. The method according to claim 10, wherein step (a) occurs prior to step (b).

* * * * *